(12) United States Patent
Heacock et al.

(10) Patent No.: US 9,974,630 B2
(45) Date of Patent: May 22, 2018

(54) LASER ORTHODONTIC DEVICES

(71) Applicant: OrthoAccel Technologies, Inc, Bellaire, TX (US)

(72) Inventors: Greg Heacock, Bellaire, TX (US); Michael K. Lowe, Bellaire, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 519 days.

(21) Appl. No.: 14/390,895

(22) PCT Filed: Apr. 12, 2013

(86) PCT No.: PCT/US2013/036289
§ 371 (c)(1),
(2) Date: Oct. 6, 2014

(87) PCT Pub. No.: WO2013/155366
PCT Pub. Date: Oct. 17, 2013

(65) Prior Publication Data
US 2015/0164618 A1    Jun. 18, 2015

Related U.S. Application Data (60) Provisional application No. 61/624,242, filed on Apr. 13, 2012, provisional application No. 61/757,288, filed on Jan. 28, 2013.

(51) Int. Cl.
| | | |
|---|---|---|
| *A61C 1/08* | (2006.01) | |
| *A61C 7/08* | (2006.01) | |
| *A61C 7/00* | (2006.01) | |
| *A61C 19/06* | (2006.01) | |
| *A61C 1/00* | (2006.01) | |

(52) U.S. Cl.
CPC .............. *A61C 7/08* (2013.01); *A61C 1/0046* (2013.01); *A61C 7/008* (2013.01); *A61C 19/066* (2013.01)

(58) Field of Classification Search
CPC ......... A61C 1/088; A61C 19/066; A61C 7/08; A61C 7/008; A61C 1/0046
See application file for complete search history.

(56) References Cited

U.S. PATENT DOCUMENTS

| | | |
|---|---|---|
| 4,244,688 A | 1/1981 | Kurz et al. |
| 4,348,177 A | 9/1982 | Kurz et al. |
| 4,382,780 A | 5/1983 | Kurz et al. |
| 5,030,098 A | 7/1991 | Branford |
| 5,487,662 A * | 1/1996 | Kipke .................. A61C 9/0006 433/215 |
| 5,554,971 A | 9/1996 | Foster |

(Continued)

FOREIGN PATENT DOCUMENTS

| | | |
|---|---|---|
| EP | 1280261 | 12/2001 |
| WO | 2006052682 | 5/2006 |

OTHER PUBLICATIONS

S Fujita, et al., Low-energy laser stimulates tooth movement velocity via expression of RANK and RANKL, Orthodontics & Craniofacial Research 11(3): 143-155, 2008.

(Continued)

*Primary Examiner* — Ralph Lewis
(74) *Attorney, Agent, or Firm* — Boulware & Valoir (57) ABSTRACT

An IR laser bite plate for orthodontic remodeling is disclosed, and the device can be combined with vibrational forces.

15 Claims, 8 Drawing Sheets

(56) References Cited

U.S. PATENT DOCUMENTS

| | | | |
|---|---|---|---|
| 5,780,958 A | 7/1998 | Strugach | |
| 5,905,837 A | 5/1999 | Wang | |
| 5,967,784 A | 10/1999 | Powers | |
| 6,347,172 B1 | 2/2002 | Keller | |
| 6,546,174 B2 | 4/2003 | Clarkin | |
| 6,632,088 B2 | 10/2003 | Voudouris | |
| 6,684,639 B2 | 2/2004 | Ichinose | |
| 6,832,912 B2 | 12/2004 | Mao | |
| 6,976,841 B1* | 12/2005 | Osterwalder | A61C 9/0006 433/29 |
| 7,029,276 B2 | 4/2006 | Mao | |
| 7,164,819 B2 | 1/2007 | Jenson | |
| 7,331,784 B2 | 2/2008 | Suzuki | |
| 7,401,961 B2 | 7/2008 | Longatti | |
| 7,511,454 B1 | 3/2009 | Legg | |
| 7,645,137 B2 | 1/2010 | Wasyluch | |
| 7,751,895 B2 | 7/2010 | Jones | |
| 8,021,148 B2* | 9/2011 | Goodson | A61C 1/088 433/29 |
| 8,029,278 B1 | 10/2011 | Levine | |
| 8,152,521 B2 | 4/2012 | Yamamoto | |
| 8,241,035 B2* | 8/2012 | Jones | A61C 17/20 433/29 |
| 2004/0110111 A1 | 6/2004 | Wasylucha | |
| 2006/0287620 A1 | 12/2006 | Tseng | |
| 2007/0103016 A1 | 5/2007 | Park | |
| 2007/0161461 A1 | 7/2007 | Nguyen | |
| 2007/0161931 A1 | 7/2007 | Kunita | |
| 2007/0179414 A1 | 8/2007 | Imboden | |
| 2007/0208284 A1 | 9/2007 | Huang | |
| 2007/0255188 A1 | 11/2007 | Tseng | |
| 2007/0299372 A1 | 12/2007 | Chang | |
| 2008/0032253 A1* | 2/2008 | Montgomery | A61C 19/066 433/29 |
| 2008/0129130 A1 | 6/2008 | Mun | |
| 2008/0227046 A1 | 9/2008 | Lowe | |
| 2008/0227047 A1 | 9/2008 | Lowe | |
| 2009/0051312 A1 | 2/2009 | Simon | |
| 2009/0058361 A1 | 3/2009 | John | |
| 2009/0224616 A1 | 9/2009 | An | |
| 2010/0055634 A1 | 3/2010 | Spaulding | |
| 2011/0103757 A1 | 5/2011 | Alkemper | |
| 2012/0214122 A1 | 8/2012 | Dwyer | |

OTHER PUBLICATIONS

Doshi-Mehtaa & W.A. Bhad-Patil, Efficacy of low-intensity laser therapy in reducing treatment time and orthodontic pain: A clinical investigation, Am J Orthod Dentofacial Orthop 2012;141 :289-97.
Michael R. Hamblin & Tatiana N. Demidova, Mechanisms of low level 5 light therapy, Proc. SPIE 6140, Mechanisms for Low-Light Therapy, 614001 (2006).
Jeffrey R. Basford, Low-Energy Laser Therapy: Controversies and New Research Findings, Lasers in Surgery and Medicine 9:1-5, Mayo Clinic, Rochester, Minnesota, 1989.
T Yoshida, Low-energy laser irradiation accelerates the velocity of tooth movement via stimulation of the alveolar bone remodeling, Orthodontics & Craniofacial Research, 12(4): 289-298 (2009).
Sugawara, Yasuyo, et al. "The alteration of a mechanical property of bone cells during the process of changing from osteoblasts to osteocytes." BONE 43.1 (2008): 19-24.
International Search Report for Counterpart PCT application dated Jun. 9, 2013.

* cited by examiner

LASER ORTHODONTIC DEVICES

PRIOR RELATED APPLICATIONS

This application is a National Phase filing of International Application PCT/US2013/036289, filed Apr. 12, 2013, which claims priority to 61/624,242, filed Apr. 13, 2012, and 61/757,288, filed Jan. 28, 2013. Each of these applications is incorporated herein by reference in its entirety.

FEDERALLY SPONSORED RESEARCH STATEMENT

Not applicable.

FIELD OF THE INVENTION

The invention relates to laser devices for correcting malocclusion, reducing pain, cleaning teeth, and the like.

BACKGROUND OF THE INVENTION

Orthodontics is a dental specialty that treats malocclusion through the movement of teeth as well as the control and modification of facial growth. This process is usually accomplished by using a continuous mechanical force to induce bone remodeling, thereby enabling the teeth to move to a better position. In this approach, orthodontic appliances provide a continuous static force to the teeth via an archwire connected to brackets affixed to each tooth or via a removable appliance such as an aligner, or some similar accessory that fits over the dentition. As the teeth slowly move due to the applied force, the force dissipates, and the archwires must be adjusted to add additional force and to continue the desired tooth movement. Although effective, this widely accepted approach takes about twenty-four months on average to achieve success.

Researchers have long postulated that a pulsating force might also be used to move teeth more rapidly and to ease the discomfort of traditional orthodontics. Mao was probably the first to prove that the use of cyclic forces could improve orthodontic straightening in rabbits (see U.S. Pat. No. 6,684,639, U.S. Pat. No. 6,832,912, U.S. Pat. No. 7,029,276). Certain dynamic loading patterns (cycling force with rest periods) were shown to greatly increase bone formation compared to static dynamic loading. Inserting rest periods is now known to be especially efficacious as it allows mechanosensitivity to be restored to the bone tissue. A point of diminishing returns is reached within each loading session. Therefore, intermittently loading force can increase the rate of bone formation significantly.

US2008227046, by OrthoAccel Technologies Inc., describes the first device specifically designed to capitalize on the Mao research and has been very successfully marketed as "AcceleDent™." This device has been shown in clinical trials to reduce patient treatment time by as much as 50% and may be the biggest advance in orthodontics since the aligner was first invented. Further, an updated model with a smoother and quieter motor (as described in US2010055634) has achieved very high patient compliance and satisfaction rates.

Although AcceleDent™ is a very successful product, there is always room for continued improvement in this field. In particular, it would be advantageous if vibration could be combined with another modality, so that remodeling is stimulated by two mechanisms of action, and infrared light may offer some possibilities in this regard.

Infrared (IR) light is electromagnetic radiation with a wavelength longer than that of visible light, measured from the nominal edge of visible red light at 0.74 micrometers (μm), and extending conventionally to 300 μm. Infrared light is used in industrial, scientific, and medical applications, and its power in medical applications has yet to be fully realized.

A laser is a device that emits light (electromagnetic radiation) through a process of optical amplification based on the stimulated emission of photons. The term "laser" originated as an acronym for Light Amplification by Stimulated Emission of Radiation. The emitted laser light is notable for its high degree of spatial and temporal coherence, unattainable using other technologies. Additionally, a laser usually produces light of a single wavelength, e.g., it is monochromatic.

Most so-called "single wavelength" lasers actually produce radiation in several modes having slightly different frequencies (wavelengths), often not in a single polarization. Therefore, the terms "monochromatic" or "single wavelength," actually includes a small range of frequencies (+/−a few percent). Further, although temporal coherence implies monochromaticity, there are even lasers that emit a broad spectrum of light, or emit different wavelengths of light simultaneously. There are some lasers which are not single spatial mode and consequently their light beams diverge more than required by the diffraction limit. However all such devices are classified as "lasers" based on their method of producing that light: stimulated emission. Lasers are employed in applications where light of the required spatial or temporal coherence could not be produced using simpler technologies.

Light Emitting diodes are another source of light that is mostly monochromatic. Strictly speaking, an LED is not a laser, although popular culture usually does not make this distinction. Lasers are closer to monochromatic, collimated (non-divergent) and coherent (wavelengths in-phase). In contrast, ordinary LED's are neither coherent nor collimated and generate a somewhat broader band of wavelengths. Another difference between the two is the power output. The peak power output of lasers is measured in watts, while that of LED's, is measured in milliwatts. Also, LED's usually have a 50% duty cycle, meaning that they are "on" 50% of the time and "off" 50% of the time regardless of what frequency (pulses per second) setting is used.

It is possible, however, to produce an LED, wherein the use of multiple semiconductor layers allows for the production of light of the same frequency and phase. Such LEDs are often called "laser diodes," indicating a higher degree of coherence and narrower frequency range.

Lasers have long been used in dentistry. For example, a dental laser is a type of laser designed specifically for use in oral surgery or dentistry. Soft tissue lasers are used to safely treat and destroy bacteria in gum pockets, preventing infection thereby allowing the gum tissue to return to a healthy state. The two soft tissue lasers commonly in use are the NdYag Laser and diode lasers.

Hard tissue lasers are also available, and are used to remove old composite fillings, repair cavities, and prepare teeth for bonding. As with soft tissue lasers, they dramatically minimize discomfort and allow the dentist to treat teeth with more precision. One laser in use is the erbium laser, which works on the hard tissues, including tooth and bone. It is of particular benefit, as providing less pain than older technology.

Other lasers have been used for imaging purposes. The Diagnodent® laser, for example, is a low level laser light which is placed against the tooth and can detect very early decay. In this small hand held device, where the laser light comes in contact with the tooth, two-way hand piece optics allows the unit to simultaneously quantify the reflected laser light energy. A clean healthy tooth structure shows little or no fluorescence, resulting in very low number readings on the display. However, carious or decayed tooth structure will emit fluorescence light, resulting in elevated number readings on the display. An audible sound is produced as well, which varies according to the amount of decay.

Lasers have also been employed in dentistry for curing purposes. Argon laser curing of traditional light-activated composite resins, for example, has been shown to be superior over conventional light-curing with respect to bond failure and chairside time, although the incidence of decalcification seems to be similar.

Finally, lasers have also been used for tooth whitening. Different types of energy can be used in this procedure, with the most common being halogen, LED, or plasma arc. Halogen light is the best source for producing optimal treatment results, and the ideal source of energy should be high energy to excite the peroxide molecules without overheating the pulp of the tooth. Lights are typically within the blue light spectrum as this has been found to contain the most effective wavelengths for initiating the hydrogen peroxide reaction.

There have also been consumer devices designed for teeth whitening. U.S. Pat. No. 7,645,137, for example, describes a hand moldable dental tray that has a light source, and can be used with a whitening gel. The device appears to only contact teeth of the upper jaws and would need to be turned over for the lower teeth, whereon the gel would have a tendency to fall out. Further, no details about the light source are provided and its connection to the tray, so it is unclear how or if the device works. U.S. Pat. No. 7,331,784 describes a light tray, which again appears to contact only the upper teeth, and an exterior blue LED connected to the tray via cable or cord and blinks during use. Since these devices are designed for teeth whitening, it may suffice to treat only the upper teeth since those are the most visible. However, neither device is suitable for orthodontic uses.

US20120214122 describes a clear mouthpiece that does contact both upper and lower teeth, together with a removable exterior portion or lightbox that has a number of blue LEDs that shine light through the clear mouthpiece and contains all of the needed circuitry. However, there is noting to guide the light and much of it will be dissipated without effect, reducing the overall efficacy of the device per unit of power consumed.

To our knowledge a laser based orthodontic remodeling device has never been proposed or achieved, nor has a portable IR laser bite plate been designed specifically for orthodontic remodeling.

SUMMARY

The disclosure generally relates to improved devices for orthodontic remodeling through the application of low level light therapy (LLLT) in a simple device that can be used by patients in the comfort of their own home, or by an orthodontist in the office. The laser can be applied via a simple extraoral power source and housing via bite plate, and can also be combined with vibratory devices such as the AcceleDent™.

Low level light is known to have therapeutic effects, and indeed has long been used to stimulate hair growth, treat skin conditions, for wound healing and inflammation, as well as to treat depression. One important point that has been demonstrated by many in vivo and ex vivo studies is that dose response is biphasic. There exists an optimal dose of light for any particular application. Doses lower than the optimum value have less effect, and doses higher than the optimum can even be harmful.

For low power visible light to have any effect on a living biological system, the photons must be absorbed by electronic absorption bands belonging to some molecular chromophore or photoacceptor. The action spectra compiled by Hamblin supports the hypothesis of the existence of cellular photoacceptors and signaling pathways stimulated by light. See FIG. 10. Clear absorption peaks are seen at 810 and 900, as well as some additional lower energy peaks in the 600 range, though little is seen in the 700 range.

Figure 11:
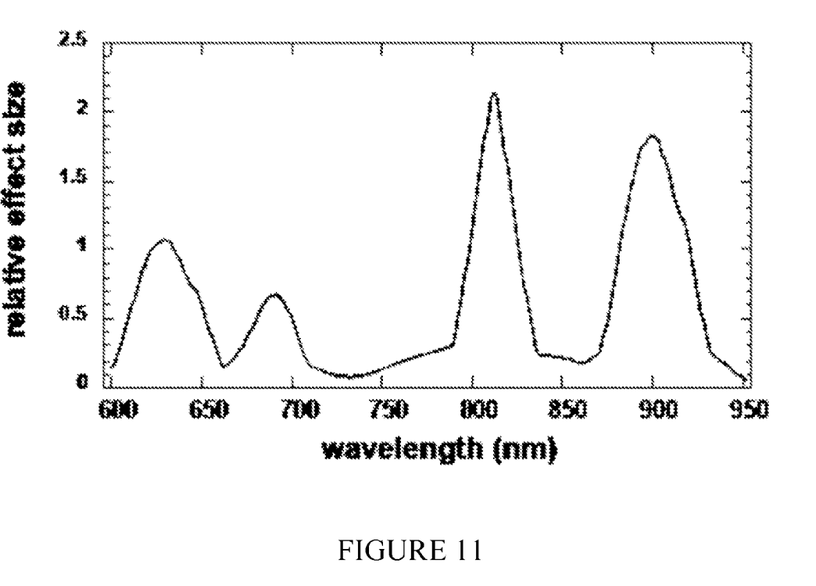
FIG. 11. Optical window in tissue due to reduced absorption of red and near-infra-red wavelengths (600-1200 nm) by tissue chromophores (from Hamblin 2006).

The second important consideration involves the optical properties of tissue. Both the absorption and scattering of light in tissue are wavelength dependent (red is much more penetrative) and the principle tissue chromophore (hemoglobin) has high absorption bands at wavelengths shorter than 600-nm. For these reasons there is a so-called "optical window" as shown in FIG. 11.

Low level light has also been successfully applied in the field of orthodontics. Work by Fujita (2008) and Yamashiro (2009) has shown that LLLT accelerated tooth movement in rats, stimulated alveolar bone remodeling, and they also concluded that low-energy laser irradiation stimulates the velocity of tooth movement via induction of RANK and RANKL. These researchers used a gallium-aluminum-arsenide (Ga—Al—As) diode laser (Osada Inc., Tokyo, Japan) with wavelength 810 nm forming continuous waves at 100 mW output power condition was used. Total energy corresponding to a 9-min exposure over the 20 days was about 54.0 J/cm$^2$, and was similar in both studies. Interestingly, Fugita's results suggests that non-coherent light was ineffective to induce remodeling or induce RANK, and that coherent light was needed. However, the LLLT field continues to debate this issue.

Researchers have now repeated these results in humans. Doshi-Mehtaa has shown that infrared radiation from a semiconductor (indium gallium arsenide) diode laser with a wavelength of 810 nm can provide an average increase of 30% in the rate of tooth movement in humans when applied on days 0, 3, 7, and 14 in the first month, and thereafter on every 15th day until complete canine retraction was achieved. See Doshi-Mehtaa, 2012.

The researchers used a split mouth design and treated twenty patients with a commercially available laser used off-label. They applied a continuous wave mode at an output power of 0.25 mW, and an exposure time of 10 seconds (energy density of 5 J per square centimeter and a total dose of 8 J), because others indicated significant bio-stimulatory effects on bone metabolism around this dosage, whereas higher dosages had bio-inhibitory effects, and lower dosage showed non-significant results. Id. Others, however have shown more stimulation using a pulsed mode laser.

Two irradiations were done on day zero, then a total of 10 irradiations were done thereafter: 5 on the buccal side and 5 on the palatal side. The laser regimen was applied on days 0, 3, 7, and 14 in the first month. Thereafter, irradiations were done on every 15th day until complete canine retraction on the experimental side.

There was a highly significant positive difference in the rates of tooth movement on the experimental side compared with the control side. The rate of tooth movement after 3 months on the experimental side showed a 1.3-fold increase, confirming earlier animal studies. The authors concluded that because low-intensity laser therapy stimulates tooth movement by altering the biologic responses, and because it does not work by increasing forces or changing mechanics, it does not tax the anchorage.

Pain was increased at day zero on both sides when braces were installed, however the authors noted a highly significant decrease in pain scores on the experimental sides on day 3 compared with day 1.

These results strongly suggest that a device that can apply a low intensity laser light to the teeth would be advantageous, and may be particularly beneficial when combined with cyclic forces, as described by US2008227046 and US2010055634. However, no such device exists and none was described in the human studies, which used a large external laser, designed for other uses.

In a first embodiment, the invention comprises an extraoral housing containing power, electronics and light source, together with optically transparent bite plate having fiber optic cable therein for transmitting the light to the teeth and surrounding periodontium, including the alveolar bone and periodontal ligament. Mirrors or other reflective surfaces can be included with the bite plate if desired to angle the emitted light in a particular direction. The bite plate should be transparent at least on the tooth and gum surfaces, although the non-teeth facing surfaces can be opaque, e.g., white or black.

In some embodiments, conventional electronics can be included within the extraoral housing, which can contain a control panel to enable the average power, energy, wave form, and pulse repetition rate to be user selected and/or allow collection and transmittal of usage data, thus allowing compliance monitoring.

In yet another embodiment, most or all of the fiber optics are omitted, and light emitting diodes ("LEDs") are fitted directly onto the bite plate. The bite plate thus comprises a core, possibly with depressions sculpted, molded or etched therein to fit diodes and wiring, one or more LEDs, and a transparent biocompatible coating to protect same.

In another embodiment, the invention generally relates to a completely intraoral laser orthodontic plate, wherein the entire device is contained in a thin, roughly planar, dentition shaped plate, and is hermetically sealed.

In its simplest embodiment, one or more LEDs (or laser diodes) are mounted on a bite plate, together with optional small battery sources, such as a coin battery and optional fiber optics, and hermetically sealed inside a translucent or transparent housing or coating. On/off switches can also be on the plate, which can be, for example, activated by biting the plate. However, the device could alternatively be wirelessly activated with an external power source, such as that described in US2009058361 and all programming components can also be external.

In many embodiments, the U shaped bite plate has phalanges (edges or rims aka a vertical surface) to contact both the buccal and lingual surfaces of the teeth and/or gums, and LEDs or fiber optics can be provided on these surfaces. In this way, radiation can be directed to the teeth and gums, or other desired treatment area. Because the LEDs are positioned directly adjacent the relevant tissues, there will be less loss and less power will be needed.

In yet other embodiments, the invention is a peel-and-stick light strip, designed to be attached to existing devices such as the Invisalign® aligners. In such embodiments, the battery and other functional components are typically contained within the strip.

Any of the devices of the invention can also contain a simple chip controlling the frequency and duration of light exposure, and this may be particularly useful with a peel-and-stick model, or a model combined with other treatment modalities, such as vibration or electrical pulses. Thus, the user can e.g., vibrate the teeth continuously for 10-20 minutes, but light be applied at its optimal interval.

Any type of laser light source can be used, including gas lasers, chemical lasers, excimer lasers, solid-state lasers, fiber lasers, photonic crystal lasers, semiconductor lasers, dye lasers, free electron lasers, bio lasers, tunable lasers and exotic laser media. However, preferred lasers are cost effective, small, and do not require cooling for use.

Preferred laser sources include semiconductor diode lasers, such as the indium gallium arsenide (InGaAs) diode, aluminum gallium arsenide (AlGaAs) semiconductor diode, but other laser sources may be used. Other 810 nm laser diodes include InGaAsP/InGaP buried heterostructure (BH) lasers, InGaAs/InGaAsP/InGaP BH lasers and the like, although aluminum is not preferred. Other laser types, for example include, Diode Pumped Solid State (DPSS) Infra-Red Lasers, diode-pumped Nd:YAG, Nd:YVO4 and Nd:YLF crystal lasers and the like.

Many companies provide laser diodes in 3.8 mm, 5.6 mm, and 9 mm TO cans, in a variety of wavelengths, and a variety of output powers, e.g. 3-130 mW. The diodes can be stand alone, or come already coupled to fiber. DFB and stabilized diodes are also available high power & ultra-narrow spectral bandwidth applications, but are probably not needed for this application. Suppliers include e.g., RPMC (sells a variety of laser diodes and solid state lasers); LaserGlow Technologies (sells Diode Pumped Solid-State (DPSS) Lasers, Collimated Diode Lasers, Low-Noise Diode Lasers, Fiber-Integrated Diode Lasers, Enhanced Profile Diode Lasers, Low-Noise DPSS Lasers, SLM DPSS Lasers, Water-Cooled HP DPSS, Q-Switched DPSS Lasers, AOM Q-Switched DPSS Lasers, Dual-Wavelength Lasers, and Triple-Wavelength Lasers). Pacer Advancing Technology has a large number of laser options, which include 810 nm laser diodes that are fiber coupled in 4 different power outputs.

Further, it may be equally or nearly equally efficacious to use LEDs instead of laser diodes, and any loss in efficacy may be offset by cost, reliability and/or power consumption characteristics. Indeed, Dr. Basford (1989) has suggested that the coherent aspect of laser may not be the source of its therapeutic effect. He states "firstly, the stimulating effects (from therapeutic light) are reported following irradiation with non-laser sources and secondly, tissue scattering, as well as fiber optic delivery systems used in many experiments rapidly degrade coherency. Thus any effects produced by low-energy lasers may be due to the effects of light in general and not to the unique properties of lasers. Under this view, laser therapy is really a form of light therapy, and lasers are important in that they are convenient sources of intense light at wavelengths that stimulate specific physiological functions. However, coherency is not essential, under this theory."

Organic light-emitting diodes (OLEDs), polymer light-emitting diodes (PLED) and electroluminescent (EL) wire may be preferred in the near future, providing costs can be reduced, and if lifespan, frequency and intensity characteristics are suitable.

Figure 10:
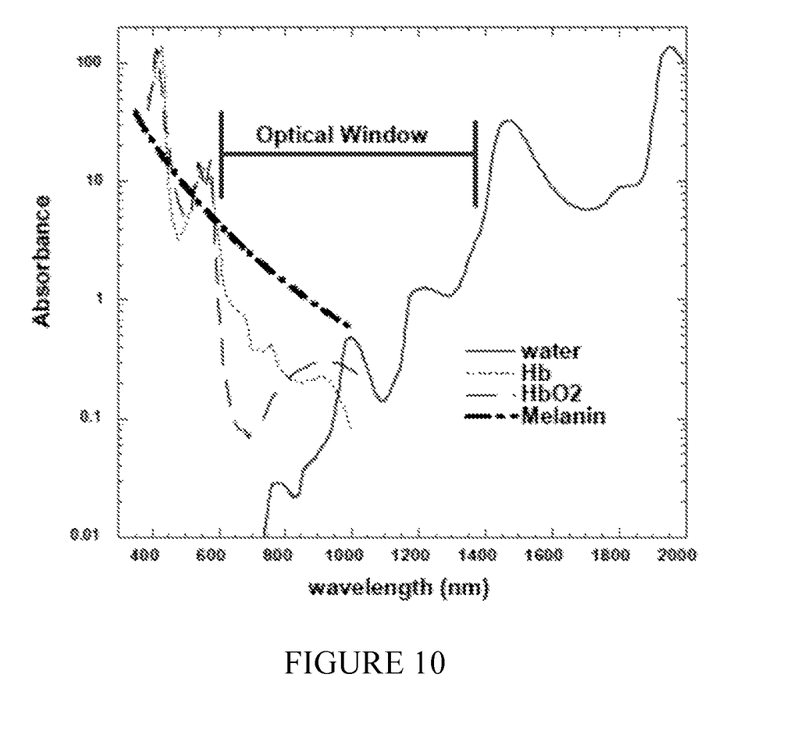
FIG. 10. Generalized action spectrum for LLLT effects in cells, animals and patients. Data shown are an amalgamation of many literature reports from multiple laboratories (from Hamblin 2006).

Preferred frequencies may be between 375 nanometers (nm) to 1800 nm, preferably from 660 and 900 nm, more preferred about 800-820 nm. In fact, 810 nm and 900 and the other peaks in FIG. 10 are particularly preferred.

Preferred output levels are about 0.1 mW to 1 mW, more preferred 0.1-0.5, even more preferably about 0.25 mW, or whatever equivalent to provide an energy density of about 1-20 or about 5 J per square centimeter per minute. The laser can be pulsed or continuous wave, and various alternative wave forms are also possible.

It may be preferred to combine an infrared frequency with visible light frequency for safety reasons. Alternatively or in addition, the device can be combined with moisture sensors, e.g., separated electrodes, so that the device can only be activated when in the wet environment of the mouth.

It is specifically contemplated that lasers of differing wavelengths can be combined, and each pulsed according to its maximal therapeutic efficacy. Thus, for example, light of about 800-900 nm can be combined with light of about 400-500 nm and such device can have both whitening and orthodontic remodeling efficacy. As another example, red, blue and green light can be combined to produce a visible white light.

The frequencies, wave form and power should be optimized for orthodontic remodeling purposes, however, a tunable laser could also be employed, thus allowing a variety of uses. For example, teeth bleaching can be achieved with or without a hydrogen peroxide bleaching agent when stimulated 980-nm diode laser at 0.8 W, or a 532-nm KTP laser at 1.0 W for 30 sec. Indeed, the patient may prefer an intraoral whitening bite plate to dental visits with the mouth held wide open for laser treatment that lasts about a half hour. For such embodiments, the blue-green spectrum of 400-500 nanometers may be preferred, as this has been found to be the most effective whitening range.

In preferred embodiments, laser orthodontic devices have the capability of recording device usage and reporting same to the orthodontic professional. Preferably these communications are wireless, e.g., via Bluetooth®, but can also be wired, and the communication can occur in the orthodontic professional's office or via the internet. In another embodiment, the orthodontic professional (and possibly patient) has the ability to modulate frequency, force, and which lasers or laser/vibrators are used (within certain safe ranges). Designing circuitry and programming for achieving these goals is well within the art.

In another embodiment, the laser is combined with the extraoral vibrator of US2008227046 and US2010055634, each incorporated by reference. In yet other embodiments, the laser can be combined with intraoral vibrators, also described in US2010055634. Preferably, the vibrator is a more stable vibrator with improved performance characteristics of decreased sound and low variability frequency and force. In particular, the improved vibrator has a noise level less than 55 dB when measured at 6 inches, a frequency at 20-40 Hz, with a variance of only 2 Hz, and a force of 0.1-0.5 Newtons, with a variance of ±0.05 N.

When combined with a vibrating component in a wholly intraoral embodiment, the smallest means of providing vibration are employed. A large number of very small vibrating motors are available, as shown in the table below, but piezoelectric motors may be preferred due to the small size, and off-set weighted motors may be preferred due to low cost and availability. Particularly preferred are the substantially planar motors where the vibration is substantially parallel to the substrate (e.g., U.S. Pat. No. 5,554,971, U.S. Pat. No. 5,780,958, US2009224616, US2008129130, US2007103016, WO0178217, each incorporated by reference).

| Company | Catalog | Size | Specifications |
|---|---|---|---|
| ELLIPTEC AG ™ | NA See U.S. Pat. No. 6,870,304 | 10 × 3 × 2 mm | 3-6 volts<br>piezoelectric motor |
| SURPLUS TRADERS ™ | MF820 | 8 × 4 mm<br>(0.315 × 0.1575 inches) | 1.5 to 4.5 VDC<br>weighted shaft |
| SURPLUS TRADERS ™ | MF918 | 0.45 × 0.16 inches | 1 VDC to 5 VDC<br>18 ohms<br>Weighted shaft |
| MOTOROLA ™ | G13566 | 0.44 × 0.18 inches | 1 VDC to 9 VDC<br>10 ohms<br>Weighted shaft |
| SURPLUS TRADERS ™ | MF835 | 0.45 × 0.24 inches | 1.3 Vdc<br>100 mA<br>Weighted shaft |
| MATSUSHITA ™ | V0296A | 0.24 inch diameter | 1.5 VDC<br>Weighted shaft |
| SURPLUS TRADERS ™ | ME235 | 0.24 × 0.5 inches | 1.5 to 3 VDC<br>62 mA<br>weighted shaft |
| PRECISION MICRODRIVES ™ | 304-002 | 4 m × 8 mm | 2.3 VDC to 3.6 VDC<br>100-120 mA<br>11000 rpm<br>Weighted shaft |
| PRECISION MICRODRIVES ™ | 308-100 | 3.4 × 8 | 2.-3.3 V, 120 mA<br>12000 rpm<br>8 mm Shaftless Vibration Motor |

In addition to electromagnetic motors and piezoelectric motors, other motor types can be used including mechanical actuators, ultrasonic motors and the like. Vibrations may be oscillating, random, directional, circular, and the like. Vibrators are well within the skill of the art, and several are described in the patent literature (and commercially available as seen above). For example, US2007299372, US2007255188, US2007208284, US2007179414, US2007161931, US2007161461, US2006287620, each incorporated by reference, describes various vibrator motors.

Batteries may drive the light source for some intraoral or extraoral embodiments, but a plug in or wirelessly activated models can also be made. Small coin batteries, alkaline or lithium, are preferred due to their small size, but hydrogen batteries may also be preferred due to their power and power density, particularly as size and cost decrease with further technological development.

For certain embodiments, a battery that can be wirelessly recharged is preferred for longer product life (e.g., US2009051312, U.S. Pat. No. 7,511,454), but in other embodiments a low cost device is manufactured that is intended to be disposable. Wirelessly rechargeable devices will of course have additional components, as needed for operability, such as the transceiver for receiving signal, and the like, but these are known in the art and not detailed herein.

In other embodiments, charged capacitors can take the place of batteries, and wirelessly rechargeable capacitors can also be used.

Any off the shelf on/off switch can be used. Particularly preferred for the intraoral device is an on/off switch with depressible activator (push button switch, rocker switch, or membrane button switch). Membrane button switches are particularly preferred as water proof, having low profile, and being reliable.

Generally speaking, the laser(s) or LED(s), and battery or other power source, optional on/off switch and circuitry, etc. are placed directly on the bite plate and hermetically sealed with no extraoral protrusions, thus allowing the most compact bite plate, preventing drooling and maximizing patient compliance. In preferred embodiments, the core may contain depressions therein for fitting various components thereinto, thus maintaining the generally planar surface of the bite plate and maintaining a thin cross section.

The bite plate (whether for the intraoral embodiment or not) should have an average thickness of less than 10 mm and preferably is less than 7, 5, 4 or 3 mm. The various components (if any) can be placed anywhere on the bite plate, but preferably in an intra-oral embodiment the switch is positioned near the molars, where good contact with teeth is easily made, and the lasers and/or vibrators are balanced on each side of the plate in a teeth and gum facing orientation.

In one embodiment, the orthodontic plate itself contains a stiff core, such as metal or rigid plastic onto which are placed the LEDs, lasers or laser diodes and/or fiber optics, optional vibrator, and optional on/off switch, battery or power source and the circuitry, etc., as needed to run the device. Other stiff core materials can also be employed including ceramic, polymers and resins. However, aluminum and steel are preferred as easy to work with, inexpensive and having some flex, although certain plastic materials, such as polycarbonate, may be preferred as inexpensive and easily molded to fit components.

Figure 9:
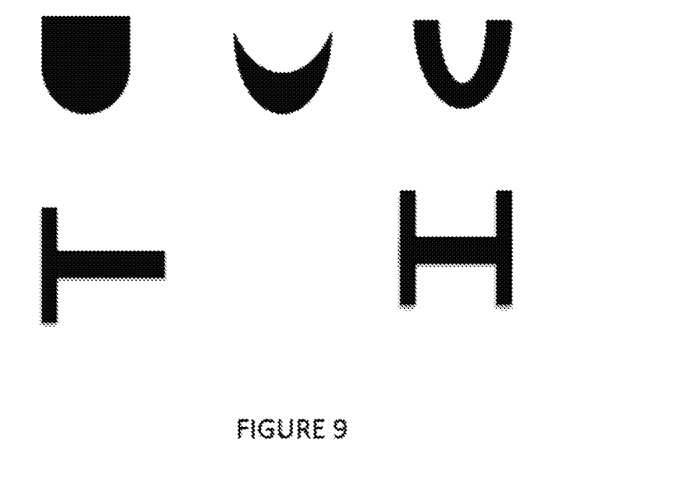
FIG. 9. Simplified representations of the U-shaped biteplate from above (top row), and in cross section (bottom row), showing the rims or phalanges, which serve to contact facial and/or lingual surfaces of teeth as well as gums, thus allowing the light to be directed thereto.

The core is generally flat and U-shaped, and the U shape can have either a hollow interior or the interior can be filled in to provide a rough semicircle (see top row in FIG. 9). The core can be completely planar, but can have edges designed to contact facial and/or lingual surfaces of teeth, as desired, thus making the bite plate having a sideways T or H shaped in cross section (see bottom row in FIG. 9). Alternatively, the edges can be provided completely or partially provided by the exterior coating, and the core is flat.

The orthodontic plate can then be covered or hermetically sealed with a transparent, liquid-tight, elastic polymeric material to protect the user's teeth from the metal, to isolate any electrical components, and to provide a biocompatible and pleasant mouth feel. Coatings, such as silicone rubber, polyurethanes, polycarbonate, cellulosics, styrene butadiene copolymers, are available in clear medical grade resins, but many more such resins may be available. Preferably, the coating will not have an objectionable taste and will be FDA approved, such as silicone rubber, and the like.

In another embodiment the bite plate coating and other parts of the appliance that contact oral tissues have a selection of flavorings for additional comfort in use of the appliance. In yet another embodiment, the device is coated with a polymer that can be reshaped for custom fit, such as boil and bite polymers, or polymers that can be activated, cured and/or set with the addition of light and/or chemicals. In yet another embodiment, the bite plate can comprise a fluoride releasing material.

Depending on which teeth or regions of dentition need to be treated, different orthodontic plate shapes are possible. However, generally, the orthodontic plate is flat to allow contact of the occlusal surfaces of all teeth and U-shaped. Alternatively, the orthodontic plate may cover only a portion of the dentition, thus being restricted to fewer teeth in use and differential tooth movement as a planned treatment approach. The orthodontic plate can also have one or more vertical edges or phalanges (perpendicular to the midline when positioned inside the mouth), said edges being positioned to contact the facial and lingual surfaces of the teeth and typically even apically beyond the gum line, thus allowing the provision of light to the gums.

In preferred embodiments, the orthodontic plate has a U-shaped bite plate, and is slightly tapered to be thinner in the back of the mouth to accommodate the hinged nature of the teeth.

The devices can be used alone, or in combination with other orthodontic devices. In some embodiments, the appliance can be used to speed boney remodeling in orthodontic uses with traditional orthodontic fixed appliances or aligner based treatments or any other appliance used for tooth movement. In other embodiments the appliance can be used to enhance boney remodeling in periodontal and oral surgical uses.

The device of the invention can be used in a variety of oral and maxillofacial applications including malocclusion, trauma repair, temporomandibular joint and muscle disorders (TMJDs), Lefort and other skeletal facial fractures, craniofacial anomalies such as boney clefts, bone defects, dentofacial deformities, dental implants, periodontal bone grafts as well as tooth, muscle, nerve, tendon, ligament, bone, and connective tissue repair.

As used herein, the term "LED" includes laser diodes.

As used herein, "monochromatic" light or light of a single wavelength e.g., 810 nm, refers to a narrow peak of light production, with the peak wavelength as indicated (e.g., 810 nm). However, some degree of peak width is accommodated, as is typical for lasers and/or laser diodes.

As used herein, reference to "the teeth" refers to all the teeth, e.g., maxillary and mandibular teeth. Thus, an edge or phalange contacting the "facial surfaces of the teeth," will contact all upper and lower teeth (except for those that are maloccluded and out of plane and possibly excepting one or more permanent molars, which can erupt quite late in development and thus are often missing in children). Where individual quadrants or upper or lower teeth are intended to be singled out, such will be specified as is standard in the art.

BRIEF DESCRIPTION OF THE DRAWINGS

FIG. 4 shows a peel and stick LED light strip, designed to be used with any existing devices, such as aligners, positioners, braces, bite plates, and the like.

FIG. 6A-C.

DETAILED DESCRIPTION

The following examples are illustrative only and not intended to limit the invention.

Figure 1:
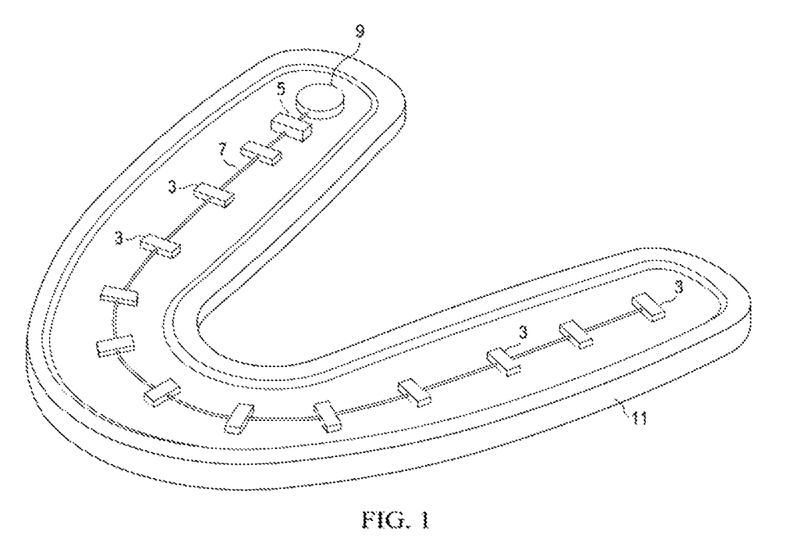
FIG. 1. Flat U shaped bite plate having LEDs thereon, plus battery and on/off rocker switch and having transparent hermetically sealed coating.

FIG. 1 shows a simple flat, U-Shaped bite plate 11 having LEDs 3 and on/off switch 5 plus wires 7 connected the LEDs 3 to the battery 9 and other components. The entirety of the bite plate 1 has a coating 11 (preferably transparent or at least IR transparent) that hermetically seals the bite plate. The user bites the plate 1, activating switch 5, so that LEDs 3 emit light, thus speeding orthodontic remodeling and reducing pain.

This simple completely intraoral embodiment can also be provided with vibrators, which can use the same or a separate on-/off switch. An separate switch may be preferred, as the time needed for light stimulation may be significantly less than the 20 minutes needed to biological response to vibration. Alternatively, a small chip embedded in the bite plate can control timing, and the same on/off switch can be used for both modes of operation.

Figure 2:
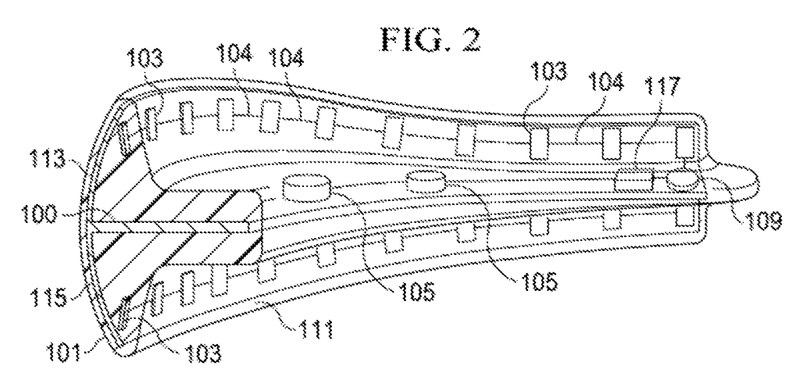
FIG. 2 Half of a bite plate shown with buccal phalange to contact buccal (cheek side) surfaces of teeth, with inner core and e.g., clear or colored coating. LEDs, wires, vibrators, battery and on/off switch are shown, as is the inner core and clear polymeric overcoat, in one prototype Versaflax CL2250.

FIG. 2 shows another intraoral variation 111, where the U-shaped bite plate (half shown) has a core 100 that also has edges 113, 115, designed to contact the buccal and facial sides of the teeth and/or gums. The upper phalange (aka edge or rim) 113 on the outer edge contacts the outer or facial surface of the upper teeth while in use, and lower phalange 115 on the outer edge contacts the outer surface of the lower teeth. The phalanges are thus roughly perpendicular to the flat U-shaped surface of the main body of the bite plate.

In this version, the LEDS 103 are placed on the tooth side (inside) surfaces of upper and lower phalanges and connected via wires 104 to battery 109 and on/off rocker switch 117. The entire plate is coated with a transparent polymer or watertight housing 101. Optional vibrators 105 are also shown.

Figure 3:
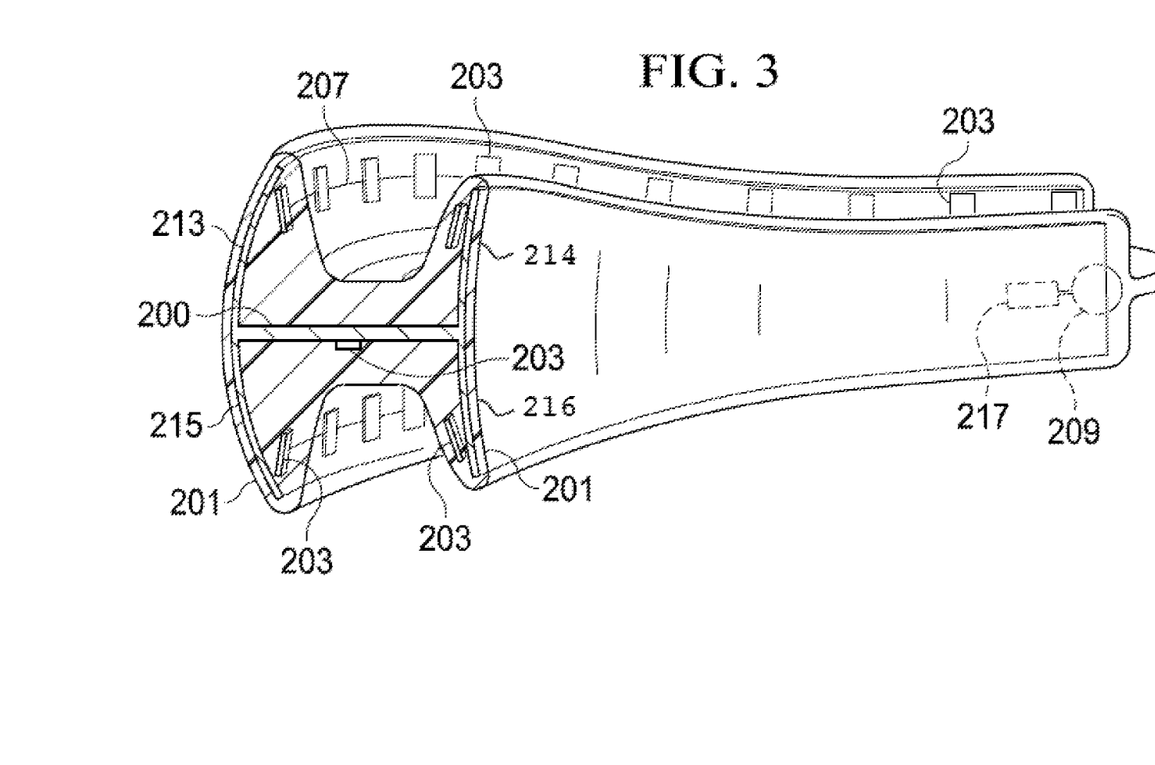
FIG. 3 Half of a bite plate shown with two phalanges to contact both buccal and lingual surfaces of teeth, with inner core and coating. LEDs, wires, battery and on/off switch also shown, together with inner core and coating.

FIG. 3 shows yet another intraoral variation, where the core 200 has phalanges 213-216 on both edges of the bite plate, thus providing a cup or trench into which the upper and lower teeth can fit. The LEDS 203 are placed on the tooth side (inside) of both of these rim surfaces, allowing the teeth and gums to be irradiated from two sides. Battery 209 is connected to on/off switch 217 and wires 207 operably connect the LEDs to these components. Coating 201 surrounds the entire bite plate sealing it against moisture.

This embodiment may be particularly useful, as it puts the light right against the gums, thus allowing maximal energy transfer to the teeth and roots. This embodiment can also be used for an at-home whitening therapy, wherein the user adds a commercial peroxide gel to both sides of the bite plate, grips same with the teeth, activates the switch and illuminates the teeth for a period of time daily or weekly, depending on need.

Such embodiment could also be beneficially combined with ultrasonic vibrators, for further teeth cleaning purposes. The on/off switched for these various components can be combined, or separate switches can be provided allowing independent activation.

Figure 4:
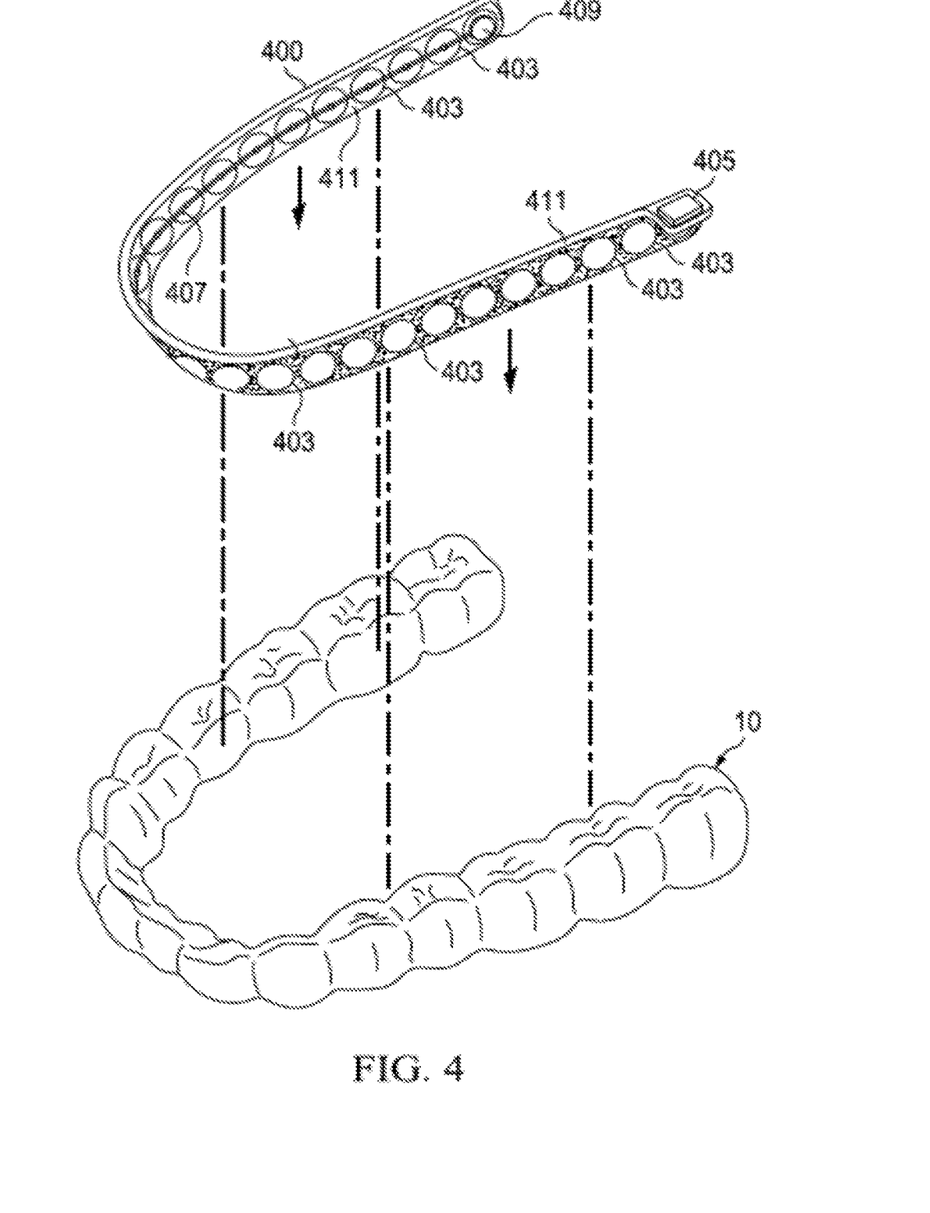

FIG. 4 shows a peel and stick light strip that can be applied to existing aligners, positioners, bite plates, and the like, thus speeding their remodeling effect. This embodiment is a simple, flexible strip having an on/off switch 405 connected via wires 407 to both LEDs 403 and battery 409. Coating 411 seals the entire device. Preferable, the coating or housing is flexible enough to allow the strip to be bent to used with various sized aligners 10, e.g., 30-70 Shore A and has a smooth lingual surface with low profile, and a flat back surface, with adhesive layer (not shown) and protective layer (not shown, but well known in the art). Peel and stick models can be particularly useful with clear aligners, being applied with a transparent FDA cleared adhesive. In such embodiments, the power of the LEDS may need to be increased somewhat to compensate for the fact that the light may have to travel through the coating, adhesive and aligner while in use.

In use, the protective strip is removed, and the light strip applied to a retainer 400 or other device or even applied directly to the teeth. We anticipate that this strip can be made inexpensively enough that the patient can purchase a dozen or so, to be used with the various aligners made throughout the course of his or her treatment. Once attached, the patient can activate the switch with the tongue, and radiate the treatment area for the desired time period, e.g., every few days, daily, or more frequently. In a variation on this theme, it is possible that the strip can be attached magnetically, rather than with adhesive, and thus be removed when not in use. Other attachments means are also possible.

Figure 5:
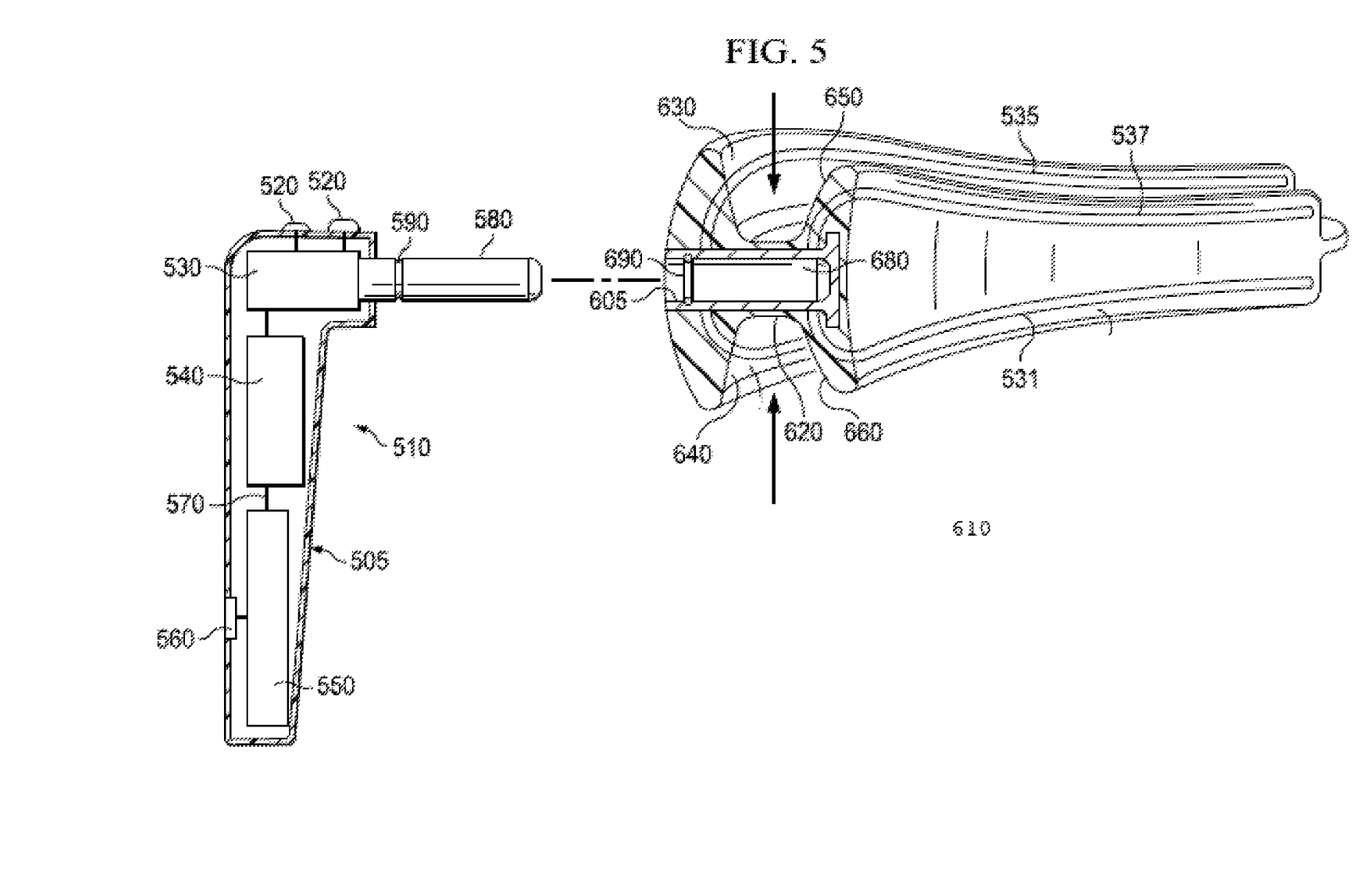
FIG. 5 shows an intraoral bite plate with extraoral light source, power and processor components operably connected together inside a housing. The bite plate detachably connects to the housing.

FIG. 5 shows a more sophisticated embodiment, which allows the user and/or practitioner to record and monitor patient usage, and can also allow selection of user parameters within an acceptably safe and efficacious range. It is well known in the art how to provide processors or chips, connectors, software, ports, display means, and the like so as to provide a user friendly controller or computer interface. Thus, these components are not detailed herein. However, our experience to date has shown that these features (the ability to monitor usage data) are particularly beneficial in encouraging patient compliance, particularly with younger patients.

FIG. 5 is a cross section of the laser device 510 and half of a bite plate 610. The laser device or driver 510 has a housing 505 containing all electronic components, except the stem 580, which protrudes therefrom, and fits into socket

680 on the bite plate. Preferably, housing 505 is water resistant or even more preferred it is waterproof or hermetically sealed. A source of light 530, which is preferably an LED, but other light sources can be used, is shown schematically as a simple box. The housing also contains battery 540, preferably a rechargeable battery and can have an optional charging port (not shown). Processor 550 captures usage data, and may also control the light source 530. Data is transmitted to a server or computer or the internet via data port or USB 560, which can also provide for battery recharging. Connections or wires 570 are shown in simple form only and not intended to convey actual wiring connections, as are on/off switches 520.

Stem 580 is shown here with depressions 590, which can circumnavigate the stem in one embodiment, but many variations of snap fitting and other connectors are possible. In addition, the stem can be on the bite plate, and the socket can be in the housing. It is preferred that the bite plate be detachable, as this allows the user to change bite plates, which may become worn, or which may no longer fit as treatment progresses.

Bite plate 610 has a hard inner core 605 that forms the socket 680 and can be any suitable shape. For example, a circle spring 690 (or any other positioning/locking mechanism) that fits into depressions 590 on stem 580 and the bite plate thus removably snap fits onto the extraoral laser device. The bite plate has the facial and lingual edges and occlusal surfaces as already described in FIG. 3. Thus, 620 is the flat surface which contacts occlusal surface of the teeth, edges 630 and 640 contact the facial tooth surfaces, while edges 650 and 660 contact the lingual tooth surfaces. The edges need not reach all the way back to permanent molars, and these erupt between 6-24 years of age, and thus are not present in many patients.

We have shown the core partially inside the lingual phalanges 537, but this can be optional depending on the flexibility of the coating, so if a less flexible material is used, the core may not be needed, as shown with phalange 535, although using a core that fits into the phalanges may simplify manufacturing, as it provides an assembly surface.

The various surfaces, 620, 630, 640, 650 and 660 can be shaped to closely follow a patient's teeth, as with an aligner, or can be simplified and fit a wide range of dentition and allow use over traditional braces. Preferably, these edges or coating thereon is made of a resilient material of durometer at least 30-80 Shore A, most preferred is a biocompatible or medical grade clear silicone of about 40 Shore A.

The light source provides the light, which is conducted throughout the bite plate via optic wires 531 which can be placed on the core or in the coating. In this simple figure, the fiber optics are shown connecting to the stem on the sides of the stem, and the requisite connector is not shown. However, it is more likely that the fiber optics will connect with the end of the stem, and usually with an off the shelf connector of suitable size. However, since space is expected to be limiting, another configuration is shown in FIG. 6, wherein the fiber optic cable is shown terminated with a connector in a stem that fits into a socket on the housing.

The processor 550 can be configured to provide a wide range of functionalities, including one or more of 1) recording usage data, 2) transmitting usage data wirelessly or via USB port or other connections, 3) wirelessly transmitting data to a smartphone application that reminds the user when to use same and/or reports usage to a parent or orthodontic professional, 4) tuning the laser frequency over an acceptable efficacious range, 5) modulating laser power or waveform over an acceptable efficacious and safe range, 6) when combined with a vibrator can allow selection of vibration frequency and power over an acceptable efficacious range, 7) provide an audible or other signal when usage time is up.

Figure 6A:
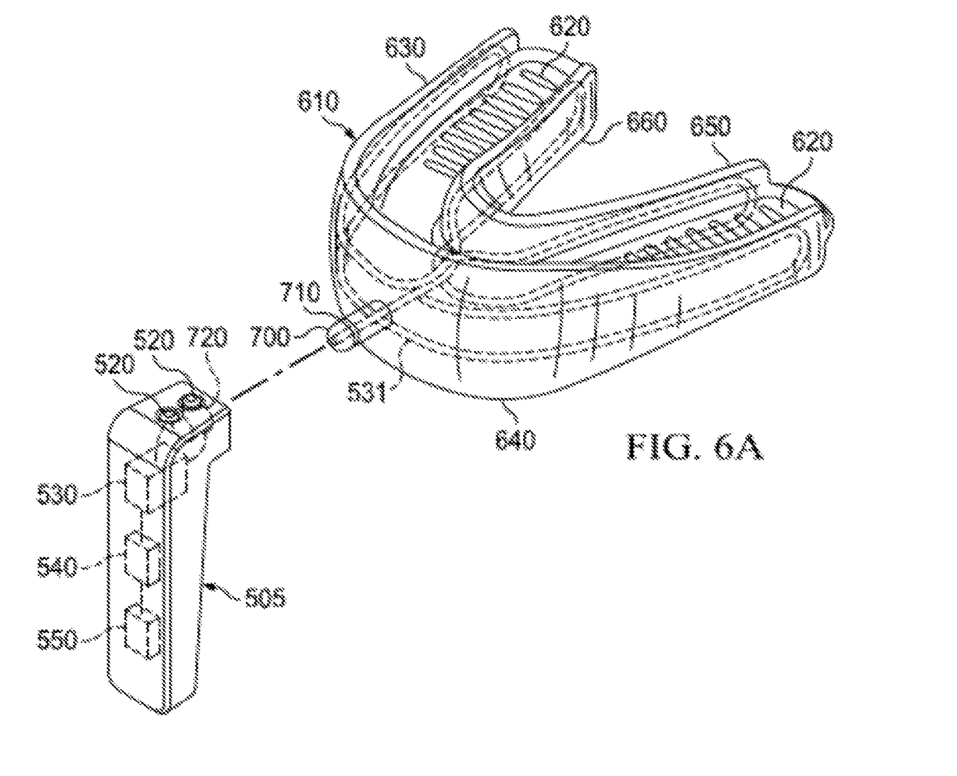
FIG. 6A shows a perspective view of the bite plate having a stem that fits into a socket in the housing.
Figure 6B:
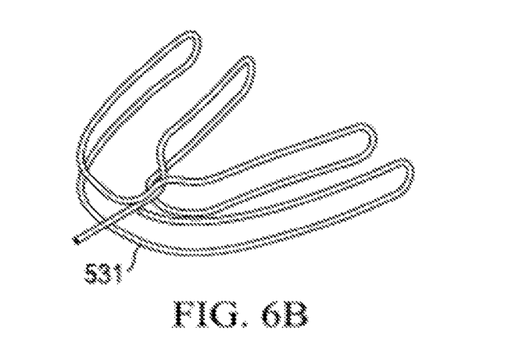
FIGS. 6B (side view) and 6C (front view) show just an approximate fiber optic layout, illustrating how a single cable can light up every tooth/gum surface of the bite plate.
Figure 6C:
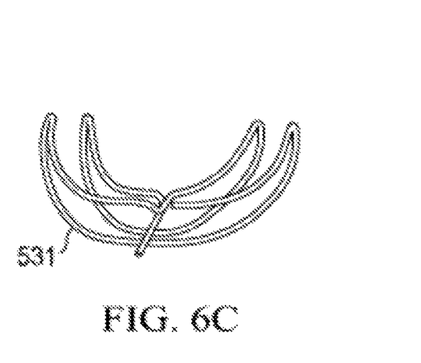

Another embodiment is shown in FIG. 6 A-C. In FIG. 6A, there is shown single side glow fiber optic cable 531 that winds back and forth over every tooth and gum facing surface. Fiber optic 531 enters stem 700 and is operably coupled to connector 710 inside stem 700. A standard connector can be used, such as a Unicam Fiber Optic Connectors, OptiSnap connectors and the like.

Stem 700 fits into a corresponding socket 720 in the housing 505, not detailed herein but having a mating and locking fit with stem 700. In this way, the light source 530 operably connects with fiber optics 531, and a single optical cable 531 is sufficient to light every tooth and gum surface. FIGS. 6B and 6C show just the optic cable for clarity.

The number and placement of optic wires can vary, however, as needed to fully illuminate the treatment area and depending on light intensity of a given cable and its bend radius. In another embodiment, the light source can also be LEDs placed directly on the core, as shown in prior figures, and as above, the device can be combined with vibrators or other treatment modalities.

In a preferred embodiment, the optical fiber is a side-glow optic cable, providing light along its entire length. Side-emitting fibers can be as simple as a single plastic or glass core without any cladding or coating. Depending on the index of refraction of the surrounding media, light sent into the core is lost through the sides because it is not trapped or internally guided. More typically, however, the plastic or glass core is clad with a different material than the core. To make the fiber "side-emitting", scattering defects are introduced into the fiber at various location. In one method, the core region is doped with small refractive and/or reflective light-scattering particles during manufacture. Alternatively, the surface of the core is modified or treated to have surface features ("defects") that scatter light out of the core. Some examples of light-emitting surface defects include serrations, notches, scratches, texture, roughness, corrugations, etching, abrasion, etc. The entire length of fiber can be modified or treated to have side-emitting properties, or just a portion of the fiber (i.e., a portion along the length or circumference of the fiber, or both). Another technique involves twisting or braiding a bundle of fibers into a "rope" which side-emits light due to the bending of the fibers. Combinations of these techniques can be used, e.g., reflective particles in the core with scratches or notches on the core's surface.

With a side-emitting optic fiber, a single cable can light up an entire surface, meaning that 4 fibers could be sufficient to light up the upper and lower buccal phalanges, and the upper and lower lingual phalanges. Alternatively, a single fiber can loop back and forth across the 4 surfaces, as shown in FIG. 6B-C, particularly thinner fibers, which have a smaller bend radius.

Side-emitting fibers are commercially available from a number of different manufacturers, e.g. Super Vision International, Inc.; Intelite, Inc.; Ashai Chemical Industry Col, Ltd., and others. A particularly preferred optic fiber might be a 2-4 mm wide optic tape, such TapeLight by Fiber Optic Products. Inc. Alternatively, a special flat, side-emitting strip can be specially manufactured for this application, or existing cables (which are typically round in cross section) can be heat flattened. A number of patents describe suitable technology, including U.S. Pat. No. 5,905,837, U.S. Pat. No.

7,164,819, U.S. Pat. No. 7,401,961, U.S. Pat. No. 6,347,172, U.S. Pat. No. 6,546,174, U.S. Pat. No. 6,347,172, US20110103757.

In yet another embodiment, the fiber optic cables can be omitted in their entirety, and the coating can be such as to itself emit light. For example, the coating can itself contain organic light-emitting diodes, or OLED and similar developing electroluminescent technology. The resulting material lights up when current is applied. In this embodiment, it may be necessary to coat the OLED containing material with a second biocompatible transparent polymer for regulatory reasons. OLED technology has yet to be fully realized, but may become practical and cost effective in the very near future. Thus, although existing prototypes are being developed with LEDs, it may be possible to provide a second generation model with this nascent technology. It may also be possible to employ EL wire in some embodiments, depending on what frequencies are desired, but at this time no IR emitting EL is easily available.

Figure 7:
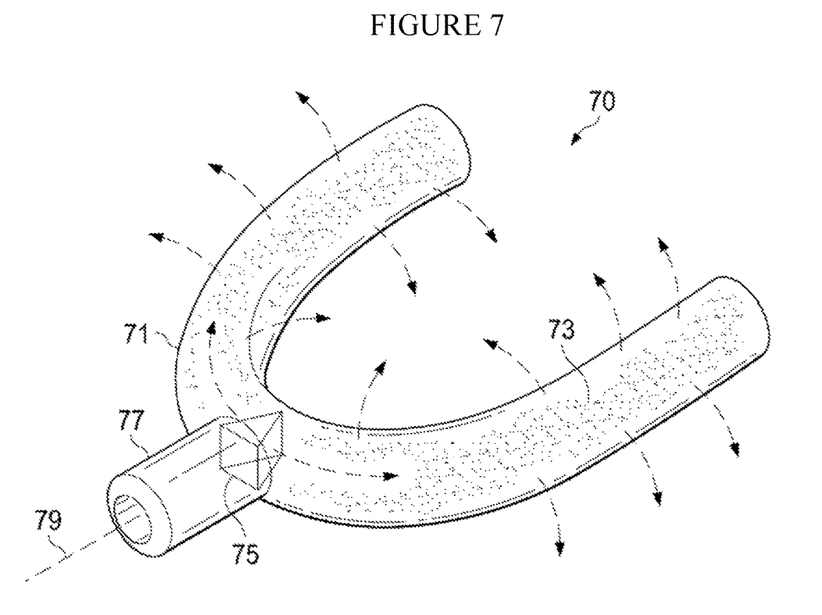
FIG. 7. A curved light pipe design.

FIG. 7 shows a curved light pipe design, wherein a light pipe 71 of transparent plastic, such as PMMA, polycarbonate or polystyrene, contains very small reflective particles 73, such as glass microspheres. The particles would act to cause the input light from laser 79 to radiate out of the light pipe 71. Within the light pipe at the connector 77 is a beamsplitter 75. This component served to direct the input light energy down each of the "legs" of the light pipe. We have shown the light source on the facial side of the bite plate, positioned centrally, but it could also be on the lingual side.

Figure 8:
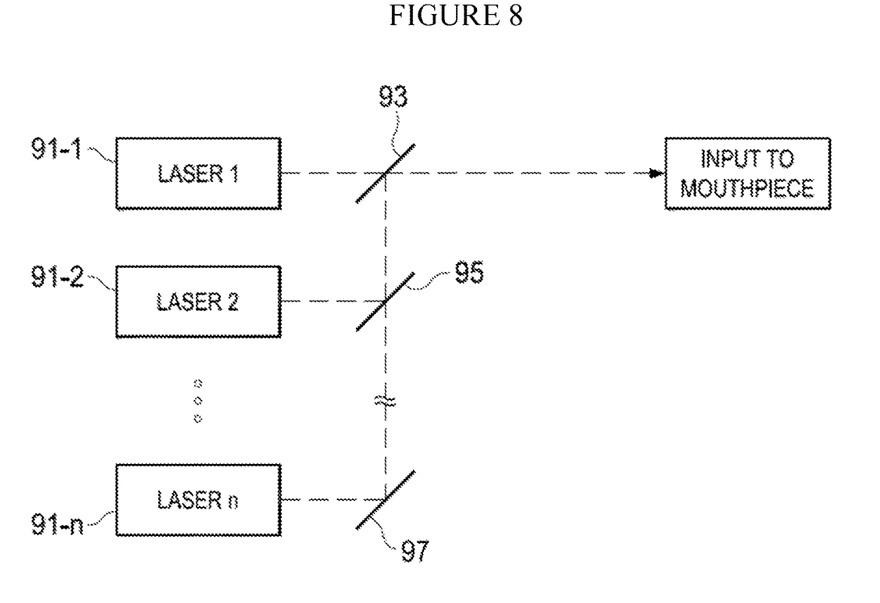
FIG. 8. A method of combining multiple wavelengths from any number of sources into a single coaxial beam.

FIG. 8 shows a method of combining multiple wavelengths from any number of sources into a single coaxial beam. This multi wavelength illumination system could be connected to a laser fiber as described in the current patent disclosure. Alternatively, this multi wavelength source could be directed into the curved light pipe in FIG. 7. In this figure, lasers or LEDs of differing wavelength 91-1, 91-2 and **91-*n* are provided. Each passes light to a multicoated glass plate 93, 95, and 97**, respectively. The glass plates are coated, as is known in the art so all to allow the three wavelengths of light to be combined and passed to the mouthpiece.

For example, if **91-*n* is a red laser, mirror 97 will reflect the red light to mirror 95, which is configured to let red light though, but reflect green light of 91-2 to mirror 93. Mirror 93 reflects both the red and green light to the mouth piece, but allows blue light from 91-1 to travel straight through, also reaching the mouthpiece. The light reaching the mouthpiece is thus a combined white light, but still retains the coherency, controllability and lower energy consumption offered by the lasers. Of course, lasers 91-1, 91-2 and 91-*n*** can be replaced by any solid state device.

The following references are expressly incorporated in their entirety:

Doshi-Mehtaa & W. A. Bhad-Patilb, Efficacy of low-intensity laser therapy in reducing treatment time and orthodontic pain: A clinical investigation, Am J Orthod Dentofacial Orthop 2012; 141:289-97.

Jeffrey R. Basford, Low-Energy Laser Therapy: Controversies and New Research Findings, Lasers in Surgery and Medicine 9:1-5, Mayo Clinic, Rochester, Minn., 1989.

Michael R. Hamblin & Tatiana N. Demidova, Mechanisms of low level light therapy, Proc. SPIE 6140, Mechanisms for Low-Light Therapy, 614001 (2006).

S Fujita, et al., Low-energy laser stimulates tooth movement velocity via expression of RANK and RANKL, Orthodontics & Craniofacial Research 11(3): 143-155, 2008.

T Yoshida, Low-energy laser irradiation accelerates the velocity of tooth movement via stimulation of the alveolar bone remodeling, Orthodontics & Craniofacial Research, 12(4): 289-298 (2009).

Mechanisms for Low-Light Therapy, edited by Michael R. Hamblin, Ronald W. Waynant, Juanita Anders, Proc. of SPIE Vol. 6140: 614001, (2006).

US2009051312, U.S. Pat. No. 7,511,454
U.S. Pat. No. 6,684,639, U.S. Pat. No. 6,832,912, U.S. Pat. No. 7,029,276
U.S. Pat. No. 4,244,688
U.S. Pat. No. 4,348,177
U.S. Pat. No. 4,382,780
U.S. Pat. No. 5,030,098
U.S. Pat. No. 5,967,784
U.S. Pat. No. 6,632,088
WO2007116654
US2008227046
US2010055634
U.S. Pat. No. 5,905,837
U.S. Pat. No. 7,164,819
U.S. Pat. No. 7,401,961
U.S. Pat. No. 6,347,172
U.S. Pat. No. 6,546,174
U.S. Pat. No. 6,347,172
US20110103757
US20040110111
U.S. Pat. No. 7,331,784
U.S. Pat. No. 8,029,278

What is claimed is:

1. A laser orthodontic device for correcting malocclusion, comprising:
   a) a bite plate being substantially U-shaped and flat to contact occlusal surfaces of teeth;
   b) said bite plate having one or more raised edges to contact lingual surfaces of teeth and gums and facial surfaces of teeth and gums;
   c) said bite plate further having an off/on switch operably coupled to a battery operably coupled to a plurality of light emitting diodes (LEDS) that emit at least one frequency of light between 700-900 nm in a range of 0.1-1 mW to provide about 5 Joule per square centimeter per minute; and
   d) said bite plate and battery and LEDS being hermetically sealed with a transparent biocompatible cover.

2. The laser orthodontic device of claim 1, comprising a stiff inner core with depressions thereon shaped to receive said battery and LEDs and a biocompatible coating over said stiff inner core.

3. The laser orthodontic device of claim 2, wherein the stiff inner core is aluminum or steel or polycarbonate.

4. The laser orthodontic device of claim 2, wherein the coating is a polyurethane polymer or silicone polymer or copolymers thereof.

5. The laser orthodontic device of claim 2, wherein the coating is custom shapeable to fit a patient's teeth.

6. The laser orthodontic device of claim 2, further comprising one or more vibrators operably coupled to said battery and inside said coating.

7. The laser orthodontic device of claim 1, where said LEDS are organic LEDS.

8. The laser orthodontic device of claim 1, where said LEDS are laser diodes.

9. The laser orthodontic device of claim 1, where said LEDS are gallium arsenide laser diodes.

10. The laser orthodontic device of claim 1, where said LEDS are aluminum gallium arsenide laser diodes.

11. A method of speeding orthodontic remodeling, comprising biting the bite plate of the device of claim 1, and activating said device for a period of time.

12. A laser orthodontic device comprising:
   a) an interoral bite plate having a substantially U-shaped surface for contacting occlusal surfaces of a patient's teeth,
   b) said U-shaped bite plate having an outside edge having upper and lower rims to contact upper and lower buccal surfaces of said teeth and said patient's gums;
   c) said U-shaped bite plate an inside edge having upper and lower rims to contact upper and lower lingual surfaces of said teeth and gums;
   d) said bite plate further comprising a power source operably coupled to an on/off switch operably coupled to a laser light source providing a light of at least one frequency between 400-1000 nm at 1-20 Joule per square centimeter per minute to each of said rims; and
   e) wherein said bite plate and power source, on/off switch and light source are hermetically sealed with a transparent covering.

13. The laser orthodontic device of claim 12, wherein said laser light source is an organic light emitting diode.

14. The laser orthodontic device of claim 12, wherein said laser light source is a laser diode.

15. An infrared orthodontic device for correcting malocclusion, comprising:
   a) a bite plate being substantially U shaped and flat to contact occlusal surfaces of teeth,
   b) said bite plate having one or more raised edges to contact lingual surfaces of upper and lower teeth and gums, and facial surfaces of upper and lower teeth and gums;
   c) said bite plate further having an off/on switch operably coupled to a battery operably coupled to a plurality of light emitting diodes (LEDS) that emit at least one frequency of infrared light in a range of 0.1-1 mW to provide about 5 Joule per square centimeter per minute; and
   d) said bite plate and battery and LEDS being hermetically sealed with a transparent biocompatible cover.

* * * * *